(12) United States Patent
Bruder et al.

(10) Patent No.: US 8,000,433 B2
(45) Date of Patent: *Aug. 16, 2011

(54) METHOD OF CREATING IMAGES IN COMPUTED TOMOGRAPHY (CT), AND CT DEVICE

(75) Inventors: Herbert Bruder, Hoechstadt (DE); Thomas Flohr, Uehlfeld (DE); Annabella Rauscher, Erlangen (DE); Karl Schwarz, Roth (DE); Karl Stierstorfer, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 1759 days.

This patent is subject to a terminal disclaimer.

(21) Appl. No.: 10/667,475

(22) Filed: Sep. 23, 2003

(65) Prior Publication Data
US 2004/0114707 A1   Jun. 17, 2004

(30) Foreign Application Priority Data
Sep. 23, 2002 (DE) ................. 102 44 181

(51) Int. Cl.
*A61B 6/03* (2006.01)
(52) U.S. Cl. .................. 378/4; 378/15
(58) Field of Classification Search ............. 378/4, 15
See application file for complete search history.

(56) References Cited

U.S. PATENT DOCUMENTS

| | | | |
|---|---|---|---|
| 5,877,337 A | | 3/1999 | Mautner et al. |
| 5,881,123 A * | | 3/1999 | Tam .................. 378/4 |
| 6,097,784 A * | | 8/2000 | Tuy .................. 378/4 |
| 6,104,775 A * | | 8/2000 | Tuy .................. 378/4 |
| 6,285,733 B1 * | | 9/2001 | Proksa et al. .......... 378/15 |
| 6,408,042 B1 | | 6/2002 | Hsieh |
| 6,529,575 B1 * | | 3/2003 | Hsieh ................. 378/4 |
| 6,839,400 B2 * | | 1/2005 | Bruder et al. ........... 378/4 |
| 7,245,755 B1 * | | 7/2007 | Pan et al. ............ 382/131 |
| 2001/0031032 A1 * | | 10/2001 | Proksa ............... 378/15 |
| 2004/0076265 A1 * | | 4/2004 | Heuscher et al. ........ 378/210 |

FOREIGN PATENT DOCUMENTS

DE    19711693 A1    11/1997

OTHER PUBLICATIONS

Tam et al., Exact (Spiral+Circles) Scan Region-of-Interest Cone Beam Reconstruction via Backprojection, 2000, IEEE Transactions on Medical Imaging, vol. 19, No. 5, pp. 376-383.*
Grass et al., 3D Cone-beam CT Reconstruction for Circular Trajectories, 2000, Physics in Medicine and Biology, vol. 45, pp. 329-347.*
Bruder et al., Performance of Approximate cone-beam reconstruction in multi-slice computed tomography, 2000, SPIE, vol. 3979, pp. 541-553.*
Sourbelle, Performance Evaluation of Exact and Approximate Cone-beam Algorithms in Spiral Computed Tomography, Mar. 25, 2002, Erlangen University, Dissertation.*
Stierstorfer et al., Segmented multiple plane reconstruction: a novel approximate reconstruction scheme for multi-slice spiral CT, Jul. 17, 2002, Physics in Medicine and Biology, vol. 47, pp. 2571-2581.*

(Continued)

*Primary Examiner* — Edward J Glick
*Assistant Examiner* — John M Corbett
(74) *Attorney, Agent, or Firm* — Harness, Dickey & Pierce, P.L.C.

(57) ABSTRACT

A method is for image reconstruction for computed tomography with a non-one-dimensional, extended detector. The rays of the detector are weighted during the backprojection as a function of their position in the beam.

15 Claims, 5 Drawing Sheets

OTHER PUBLICATIONS

Stierstorfer et al., Weighted FBP—a simple approximate 3D FBP algorithm for multislice spiral CT with good dose usage for arbitrary pitch, May 19, 2004, Physics in Medicine and Biology, vol. 49, pp. 2309-2218.*

Yan et al., Cone beam tomography with circular, elliptical and spiral orbits, 1992, Physics in Medicine and Biology, vol. 37, No. 3, pp. 493-506.*

Manzke et al., Extended Cardiac Reconstruction (ECR): A helical cardiac cone beam reconstruction method, Jul. 4, 2003, Proceedings of the VIIth International Conference on Fully 3D Reconstruction in Radiology and Nuclear Medicine.*

Chinese Office Action, Mar. 2007.

Henrik Turbell, "Cone-Beam Reconstruction Using Filtered Backprojection", Department of Electrical Engineering Linköpings Univ., Linköping, Sweden, 2001, pp. 31-40, 77-79, 84-99; Others.

Schaller Stefan et al., "Spiral Interpolation Algorithm for Multislice Spiral CT—Part I: Theory", IEEE Trans. on Medical Imaging, vol. 19, No. 9, Sep. 2000, pp. 822-834; Others.

* cited by examiner

METHOD OF CREATING IMAGES IN COMPUTED TOMOGRAPHY (CT), AND CT DEVICE

The present application hereby claims priority under 35 U.S.C. §119 on German patent application number DE 102 44 181.2 filed Sep. 23, 2002, the entire contents of which are hereby incorporated herein by reference.

FIELD OF THE INVENTION

The invention generally relates to a method of creating images in computed tomography. Preferably, it relates to one in which an object under examination is scanned with the aid of a beam originating from a focus and a non-one-dimensional detector array, and the output data determined is filtered in a suitable way and backprojected in order to obtain at least one slice which represents the absorption values of the section of the object under examination. Furthermore, the invention generally relates to a CT device which is suitable for carrying out this method.

BACKGROUND OF THE INVENTION

Methods have become known under the term "filtered backprojection" but, as 3D methods, that is to say in conjunction with a matrix-like detector array, do not furnish an image quality which is judged to be adequate in practice. This is because what are known as "cone beam artefacts" occur, because of the conical x-ray beam.

In addition, the disadvantage with this method is that redundant data, such as are produced during spiral scanning with low table advance as a result of multiple irradiation of one and the same voxel, is not used. This results in the radiation dose administered to the object under examination being used only incompletely for imaging.

Furthermore, there are thoughts relating to proceeding, in conjunction with 2D methods for image reconstruction, in such a way that preliminary images are calculated in large numbers by means of "filtered backprojection" from initial data which originates from sections of the focal path which are intrinsically inadequate for image reconstruction, with the preliminary images being reformatted to form a final slice only in a second step. These 2D methods are less useful for detector arrays with a large width, that is to say a great extent in the direction of the system axis. This is because an extremely large number of preliminary images then have to be processed, which is a problem even when high computing power is available.

In all the aforementioned methods, the problem arises that, because of possible data redundancy which occurs during the scanning of the object under examination, image artefacts are produced which have a detrimental influence on the image quality.

SUMMARY OF THE INVENTION

An embodiment of the invention is based on an object of specifying a method which permits the image quality to be increased.

According to an embodiment of the invention, this object may be achieved by a CT method and/or device.

The inventors, in one embodiment, have discovered that in image processing, it is firstly necessary to take account of the redundancies which occur with respect to a respectively considered voxel in the region under examination, in particular during the backprojection of the filtered data. Secondly, however, it is also necessary to take into account how the ray is positioned in the beam. For example, it has a decisively positive effect on the image quality if rays which are located centrally, based on the extent of the beam in the direction of the axis of rotation, are taken more into account when creating the image than rays which are positioned only marginally in relation to the beam, based on the same extent.

Accordingly, in one embodiment, the inventors propose an improved method for creating images in computed tomography which has the following steps:

rotating at least one focus, to scan an object under examination with a beam originating from the at least one focus, relative to the object on at least one focal path running around the object, wherein a detector array including a plurality of distributed detector elements is adapted to detect rays of the beam and is adapted to supply initial data representing an attenuation of the rays passing through the object under examination;

the initial data is filtered, the filtered initial data is then backprojected three-dimensionally in order to produce at least one slice of a layer of the object under examination which has a layer thickness, the slice representing absorption values, obtained from the initial data, of the voxels belonging to the layer of the object under examination for the radiation of the beam, and during the backprojection, the rays are weighted as a function of their position in the beam.

In a particular embodiment, the filtering is carried out in the direction of the tangent to the focal path belonging to the respective focal position. It has been shown that, with this filtering direction, a particularly high image quality can be achieved. The selection of this filtering direction is based on the finding that the abovedescribed 2D method permitting a high image quality and based on preliminary images would, so to speak, change into a 3D method if the sections of the focal path on which the calculation of preliminary images is based were to be shortened so severely that they would cover only a single projection whose data would then be filtered in the direction of the tangent to the focal path, and in that it would then be possible to expect that such a 3D method would then permit a comparatively good image quality as the 2D method.

If the beam has an extent in the direction of rotation and an extent in the direction of the axis of rotation, then it is advantageous to weight rays which are arranged centrally in the beam, as based on the extent of the beam in the direction of the axis of rotation, to a greater extent than the rays which are arranged close to the edge in the beam, as based on the extent of the beam in the direction of the axis of rotation.

The detector preferably used is a non-one-dimensional detector array. This is because basically the weighing has been developed for the case where the so-called cone-beam angle is large enough. This angle gets large if the detector has a certain length also in the direction of the rotational axis (z), or, in other words, if the detector has many (16 or 32 for example) parallel rows of elements. The detector is then area-like.

The method according to an embodiment of the invention may then be carried out particularly easily if, before filtering, a conversion of the initial data obtained in fan beam geometry in the form of rays $P(\alpha, \beta, q)$ into parallel data present in parallel beam geometry in the form of rays $P(\theta, \beta, q)$ (azimuthal "rebinning") or $P(\theta, p, q)$ (complete "rebinning", that is to say azimuthal and radial "rebinning") is performed. In this case, with reference to FIG. 3

$\alpha$ is the focal angle

β is the fan angle q is the row index of the detector system corresponding to the z coordinate, θ=α+β is the parallel fan angle, p=$R_F$ sin(β) is the parallel coordinate corresponding to the distance of the ray from the axis of rotation (system axis), and $R_F$ is the radius of the focal path.

According to a preferred embodiment of the invention, the backprojection of the parallel data is carried out in that, in the course of the backprojection for each voxel V(x,y,z), for each θ∈[o, π] for the rays P(θ+kπ, β̃, q) and P(θ+kπ, p̃, q) whose projection along the system axis goes through (x,y), the sum $$P_{x,y,z}(\theta) = \sum_k \sum_q W \cdot h\left(d_{x,y,z}\left(\theta + k\pi, \left\{\begin{matrix}\tilde{p}\\ \tilde{\beta}\end{matrix}\right\}, q\right)\right) \cdot P\left(\theta + k\pi, \left\{\begin{matrix}\tilde{p}\\ \tilde{\beta}\end{matrix}\right\}, q\right)$$

is formed, where x,y,z are the coordinates of the respective voxel V(x,y,z), k is a whole number corresponding to the number of half revolutions of the focus included in the reconstruction, p̃ are the parallel coordinates of those rays whose projections along the system axis run through the coordinates (x,y) of the respective voxel V(x,y,z), β̃ are the fan angles of those rays whose projections along the system axis run through the coordinates (x,y) of the respective voxel V(x,y,z), h is a weighting function determining the layer thickness of the layer of the object under examination represented in the slice produced, d is a function which is equal to the distance of the respective ray from the corresponding voxel V(x,y) and or is dependent on the distance of the respective ray from the corresponding voxel V(x,y), and W represents a weighting function which weights rays with a large parallel fan angle θ less than rays with a small parallel fan angle θ.

In this case, the notation $$\left\{\begin{matrix}\tilde{p}\\ \tilde{\beta}\end{matrix}\right\}$$

expresses the fact that the formation of the sum can optionally be carried out for rays obtained by way of azimuthal "rebinning" or complete "rebinning", the filtering tangential to the focal path in the case of azimuthal "rebinning" being filtering in the β direction and, in the case of complete "rebinning", being filtering in the p direction.

Because of the summing both over k and over q, it is then ensured that all the rays running through one and the same voxel are taken into account and the radiation dose supplied to the object under examination is thus used completely.

A particularly preferred embodiment provides that, for the purpose of the backprojection of the parallel data, the sum $$H = \sum_k \sum_q W \cdot h\left(d_{x,y,z}\left(\theta + k\pi, \left\{\begin{matrix}\tilde{p}\\ \tilde{\beta}\end{matrix}\right\}, q\right)\right)$$

normalized to the sum H of the weights h $$P_{x,y,z}(\theta) = \frac{1}{H}\sum_k \sum_q W \cdot h\left(d_{x,y,z}\left(\theta + k\pi, \left\{\begin{matrix}\tilde{p}\\ \tilde{\beta}\end{matrix}\right\}, q\right)\right) \cdot P\left(\theta + k\pi, \left\{\begin{matrix}\tilde{p}\\ \tilde{\beta}\end{matrix}\right\}, q\right)$$

is formed. This procedure permits an image quality which is improved again, since possible overemphasis of voxels which are struck by more rays than other voxels is eliminated, and thus corresponding artefacts are avoided. The CT value of the respective voxel is obtained by summing over θ.

According to an embodiment of the invention, the weighting function can be a function of the parallel fan angle with W(θ+kπ), and preferably represent a smooth function which has the value 1 for central rays, as based on the extent of the fan of rays in the direction of the axis of rotation or z direction, and tends to 0 for marginal rays.

If the detector array has detector elements arranged in the manner of rows, then the weighting can be represented by a function of the row number W(q), a smooth function also preferably being used here which, for rays with a centrally placed detector row or a plurality of centrally placed detector rows, has a high value, preferably the value 1, and for rays arranged at the margin tends to 0; for example this can be a $\cos^2$ function.

The method according to an embodiment of the invention can be used, for example when, according to one variant of the invention, the focal path is a circular path (tomogram scanning). According to a preferred variant of the invention, however, the focal path is a spiral path, which is brought about by the focus being moved on a circular path about the system axis and, at the same time, there being a relative movement between focus and object under examination in the direction of the system axis. On the basis of such spiral scanning, even relatively large volumes of the object under examination can be examined without problems.

In the case of tomogram scanning, k is normally k=1 or k=2; in the case of spiral scanning, k is selected while taking account of the relative displacement in the direction of the system axis carried out per full revolution, such that the region to be imaged of the object under examination is registered completely.

According to the basic idea of an embodiment of the invention, the inventors also propose to improve a CT device for scanning an object under examination with a beam originating from at least one focus and with a non-one-dimensional detector array having a large number of distributed detector elements for detecting the rays of the beam, the at least one focus moving relative to the object under examination on at least one focal path running around the object under examination with the opposite detector array, to the effect that at least means for collecting detector data, filtering and backprojection are provided, which carry out the method described above, these steps preferably and as far as possible being implemented by programs or program modules.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
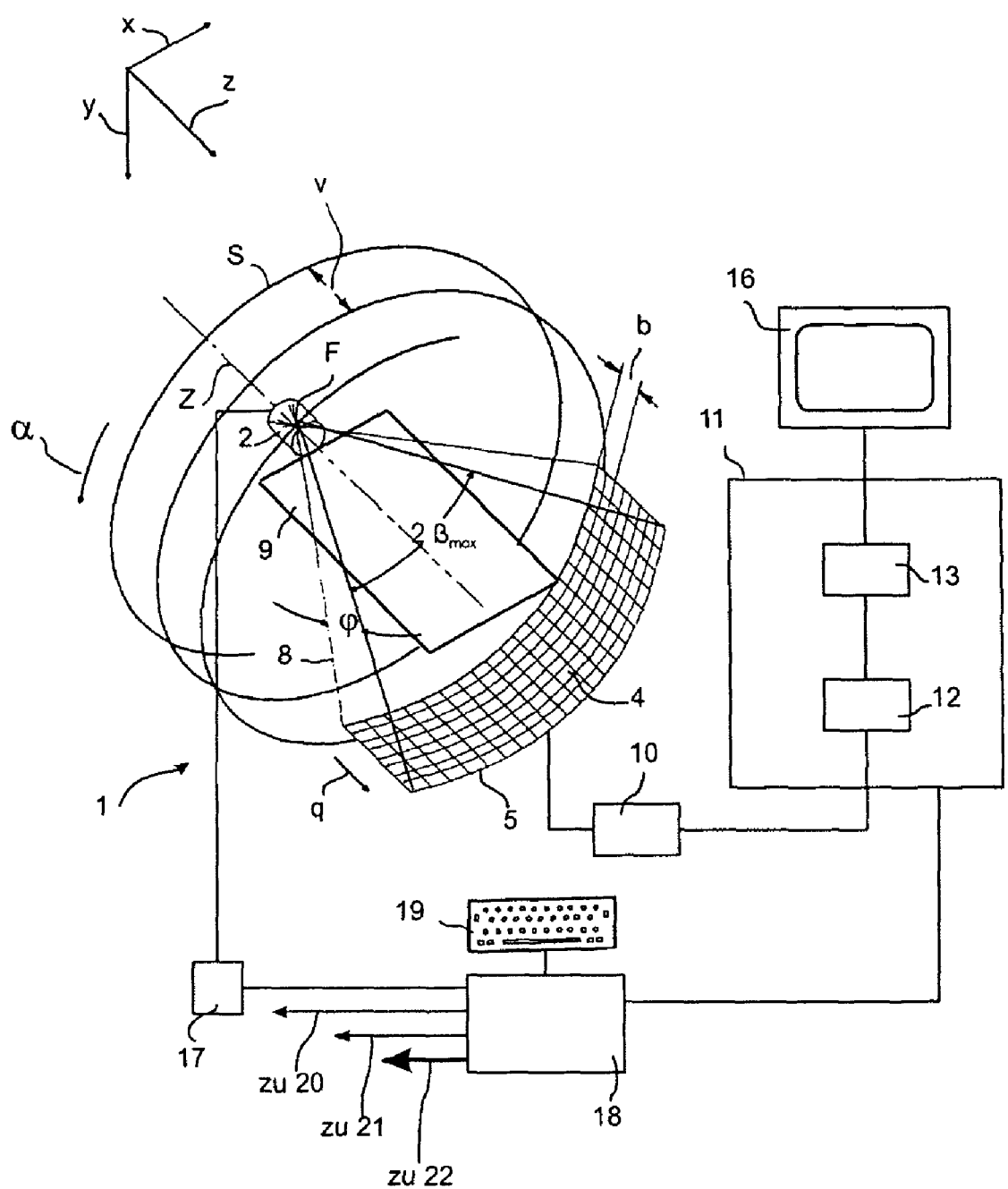
FIG. 1 shows a CT device having a plurality of rows of detector elements in a partly perspective, partly block-diagram illustration.
Figure 2:
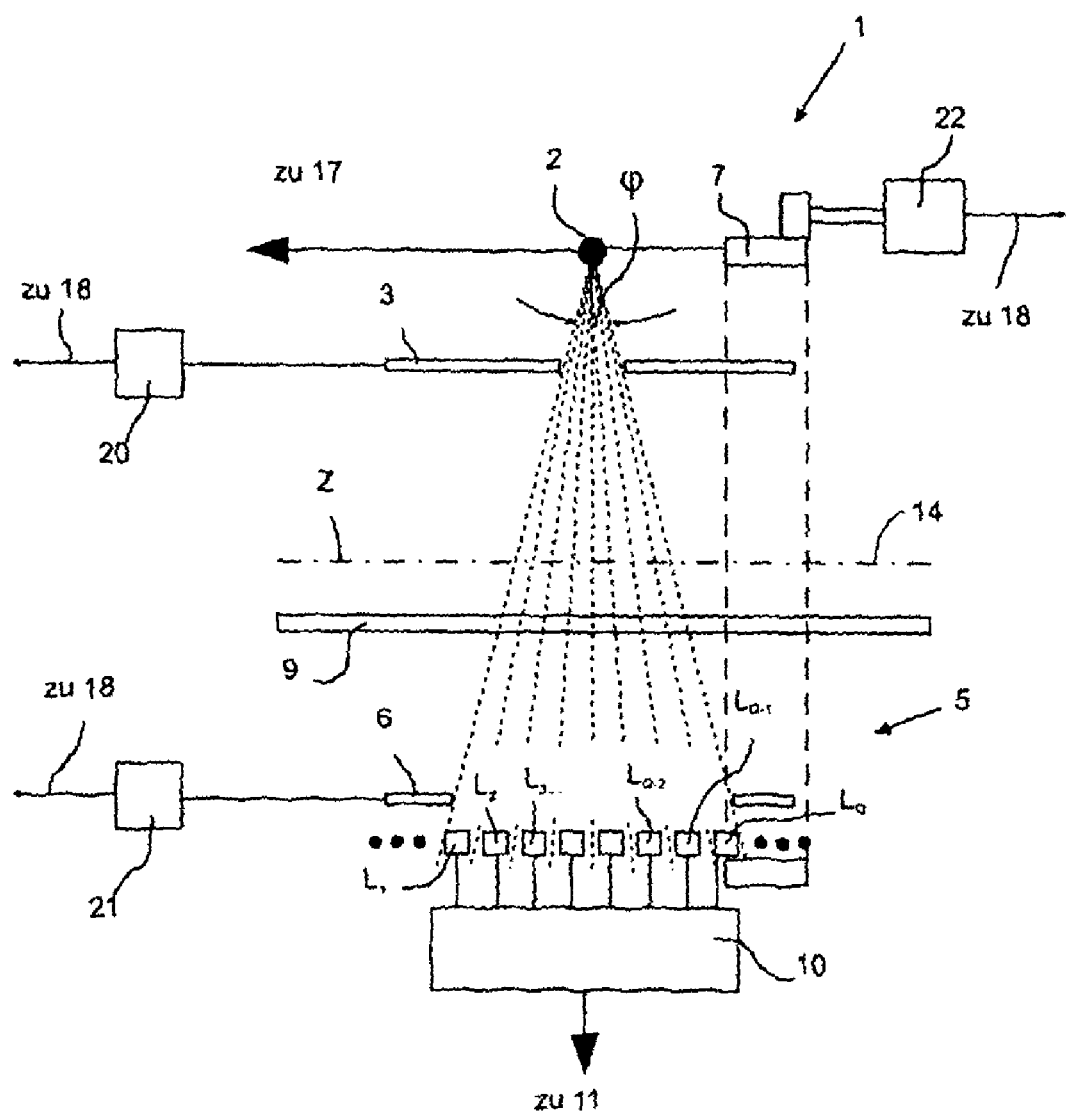
FIG. 2 shows a longitudinal section through the device according to FIG. 1.

FIGS. 1 and 2 illustrate a CT device of the third generation suitable for carrying out the method according to an embodiment of the invention. Its measurement arrangement, designated overall by 1, has an x-ray source, designated overall by 2, with a beam aperture stop 3 arranged in front of the latter, close to the source (FIG. 2). A detector system 5 is formed as a two-dimensional array of a plurality of rows and columns of detector elements—one of these is designated 4 in FIG. 1—with a beam aperture stop 6 in front of the latter, close to the detector (FIG. 2) in FIG. 1. For clarity, only eight rows of detector elements 4 are shown. However, as indicated by dots in FIG. 2, the detector system 5 has further rows of detector elements 4.

The x-ray source 2 with the aperture stop 3, on the one hand, and the detector system 5 with the aperture stop 6, on the other hand, are fitted, in the manner which can be seen from FIG. 2, to a rotary frame 7. They are fitted opposite each other in such a way that a pyramidal x-ray beam originating from the x-ray source 2 during operation of the CT device and masked by the adjustable aperture stop 3, whose marginal rays are designated 8, strikes the detector system 5. In this case, the aperture stop 6 is adjusted in accordance with the cross section of the x-ray beam set by the aperture stop 3 such that only that region of the detector system 5 which can be struck directly by the x-ray beam is exposed. In the operating mode illustrated in FIGS. 1 and 2, these are eight rows of detector elements 4, which are referred to as active rows in the following text. The further rows, indicated by dots, are covered by the aperture stop 6 and therefore not active.

Each row of detector elements 4 has a number K of detector elements, $\beta_k = \beta_1$ to $\beta_K$ being the channel index and each detector element being assigned a fan angle $\beta_k$. The fan angle of the central detector element is equal to 0; the fan angles of the two outermost detector elements are $\beta_1 = +\beta_{max}$ and $\beta_K = -\beta_{max}$.

The active rows $L_q$ of detector elements 4 are designated $L_1$ to $L_Q$, q=1 to Q being the row index which, in the case of the exemplary embodiment described, corresponds so to speak to the z coordinate.

The x-ray beam has the cone angle $\phi$ plotted in FIGS. 1 and 2, which is the opening angle of the x-ray beam in a plane containing the system axis Z and the focus F. The opening angle of the x-ray beam in a plane at right angles to the system axis Z and containing the focus F (fan opening angle) is $2\beta_{max}$ and is plotted in FIG. 1.

The rotary frame 7 can be set rotating by way of a drive device 22 about a system axis designated by Z. The system axis Z runs parallel to the z axis of a three-dimensional rectangular coordinate system illustrated in FIG. 1.

The columns of the detector system 5 likewise run in the direction of the z axis, while the rows, whose width b is measured in the direction of the z axis and is 1 mm, for example, run transversely with respect to the system axis Z and the z axis.

In order to be able to move an object under examination, for example a patient, into the beam path of the x-ray beam, a mounting device 9 is provided. This can be displaced parallel to the system axis Z, that is to say in the direction of the z axis. To be specific, it can be displaced in such a way that there is synchronization between the rotational movement of the rotary frame 7 and the translational movement of the mounting device. The effect is that the ratio between translation and rotational speed is constant, this ratio being adjustable by a desired value for the advance v of the mounting device per revolution of the rotary frame being selected.

It is therefore possible for a volume of an object under examination located on the mounting device 9 to be examined in the course of a volume scan, it being possible for the volume scan to be carried out in the form of spiral scanning. The effect is that, with simultaneous rotation of the measuring unit 1 and translation of the mounting device 9, a large number of projections from different projection directions are recorded by the measuring unit for each revolution of the measuring unit 1. During the spiral scanning, the focus F of the x-ray source moves relative to the mounting device 9 on a spiral path designated S in FIG. 1. The spiral scanning must extend in the $\alpha$ direction over at least $\pi + 2\beta_{max}$, in order to permit the complete reconstruction of a CT image for each row of detector elements, but can also be longer as desired within the technical limits of the CT device.

However, because of the fact that a plurality of rows of detector elements 4 are present, a volume of the object under examination can also be examined in the course of what is known as a tomogram scan, in which no relative movement takes place in the direction of the z axis between the measuring unit 1 and mounting device 9 (v=0). In the case of the tomogram scan, the size of the volume examined is therefore determined by the number of active rows of detector elements 4. During a tomogram scan, the focus F moves on a circular focal path which lies in a plane designated the mid-plane below.

The tomogram scanning can be carried out in the form of a part revolution or in the form of a complete revolution, the part revolution covering a part revolution interval of at least $\pi + 2\beta_{max}$ (half a revolution plus the fan opening angle), which permits complete reconstruction of a CT image, while a full revolution covers $2\pi$.

The measured data read out in parallel from the detector elements of each active row of the detector system 5 during the spiral or tomogram scanning and corresponding to the individual projections $P(\alpha, \beta, q)$ in fan beam geometry is subjected to digital/analog conversion in a data conditioning unit 10, serialized and transmitted to an image computer 11.

Following preconditioning of the measured data in a preconditioning unit 12 belonging to the image computer 11, the resultant data stream passes to a slice reconstruction unit 13. This unit 13 uses the measured data to reconstruct slices of desired layers of the object under examination in accordance with a method according to an embodiment of the invention based on "filtered backprojection", yet to be described in detail.

The CT images are composed of pixels (pixel=picture element) assembled in the manner of a matrix, the pixels being assigned to the respective image plane. Each pixel is assigned a CT number in Hounsfield units (HU). The individual pixels are displayed in accordance with a CT number/gray value scale in a gray value corresponding to their respective CT number.

In this case, each pixel illustrates a voxel (voxel=volume element) of the layer illustrated in the CT image and belonging to the object under examination. Since, because of the multiplicity of rows of the detector system 5 and, if appropriate, the spiral scanning, measured data with respect to a plurality of layers of the object under examination is obtained, 3D data is available. This is subjected to 3D backprojection within the context of the invention.

As the final result, 3D image data is available in the form of a three-dimensional matrix, for example with the axes x,y,z, each element in the matrix corresponding to a voxel V(x,y,z) and containing the gray value corresponding to the associated CT number. Those elements of the three-dimensional matrix which have the same x,y, or z value then in each case represent a planar slice of the layer of the object under examination corresponding to the defining x,y, or z value.

The images reconstructed by the slice reconstruction unit 13 are displayed on a display unit 16, for example a monitor, connected to the image computer 11.

The x-ray source 2, for example an x-ray tube, is supplied with the necessary voltages and currents, for example the tube voltage U, by a generator unit 17. In order to be able to set these to the respectively necessary values, the generator unit 17 is assigned a control unit 18 with keyboard 19. This permits the necessary adjustments.

In addition, the other operation and control of the CT device is carried out by way of the control unit 18 and keyboard 19. This is illustrated by the fact that the control unit 18 is connected to the image computer 11.

Inter alia, the number Q of active rows of detector elements 4, and therefore the position of the aperture stops 3 and 6, can be adjusted. For this purpose, the control unit 18 is connected to adjusting units 20 and 21 assigned to the aperture stops 3 and 6. Furthermore, the rotation time T needed by the rotary frame 7 for a complete revolution can be adjusted. This is illustrated by the fact that the drive unit 22 assigned to the rotary frame 7 is connected to the control unit 18.

Although it is possible in principle to implement the method according to an embodiment of the invention in fan beam geometry as well, the CT device described is preferably operated in a mode in which the method according to an embodiment of the invention is implemented in parallel beam geometry.

Accordingly, the data obtained during the scanning of the region of the body of the patient which is relevant to the respective examination by way of spiral or tomogram scanning in fan beam geometry is first of all converted, in a manner known per se, into data in parallel beam geometry by way of a method generally designated "rebinning". This conversion is based on resorting the data obtained in fan beam geometry in such a way that rays are removed from different projections recorded in fan beam geometry, and joined together to form a projection in parallel beam geometry. In parallel beam geometry, data from an interval with a length $\pi$ is sufficient to be able to reconstruct a complete image. In order to obtain this data, data in fan beam geometry from an interval of length $\pi+2\beta_{max}$ must nevertheless be available.

Figure 3:
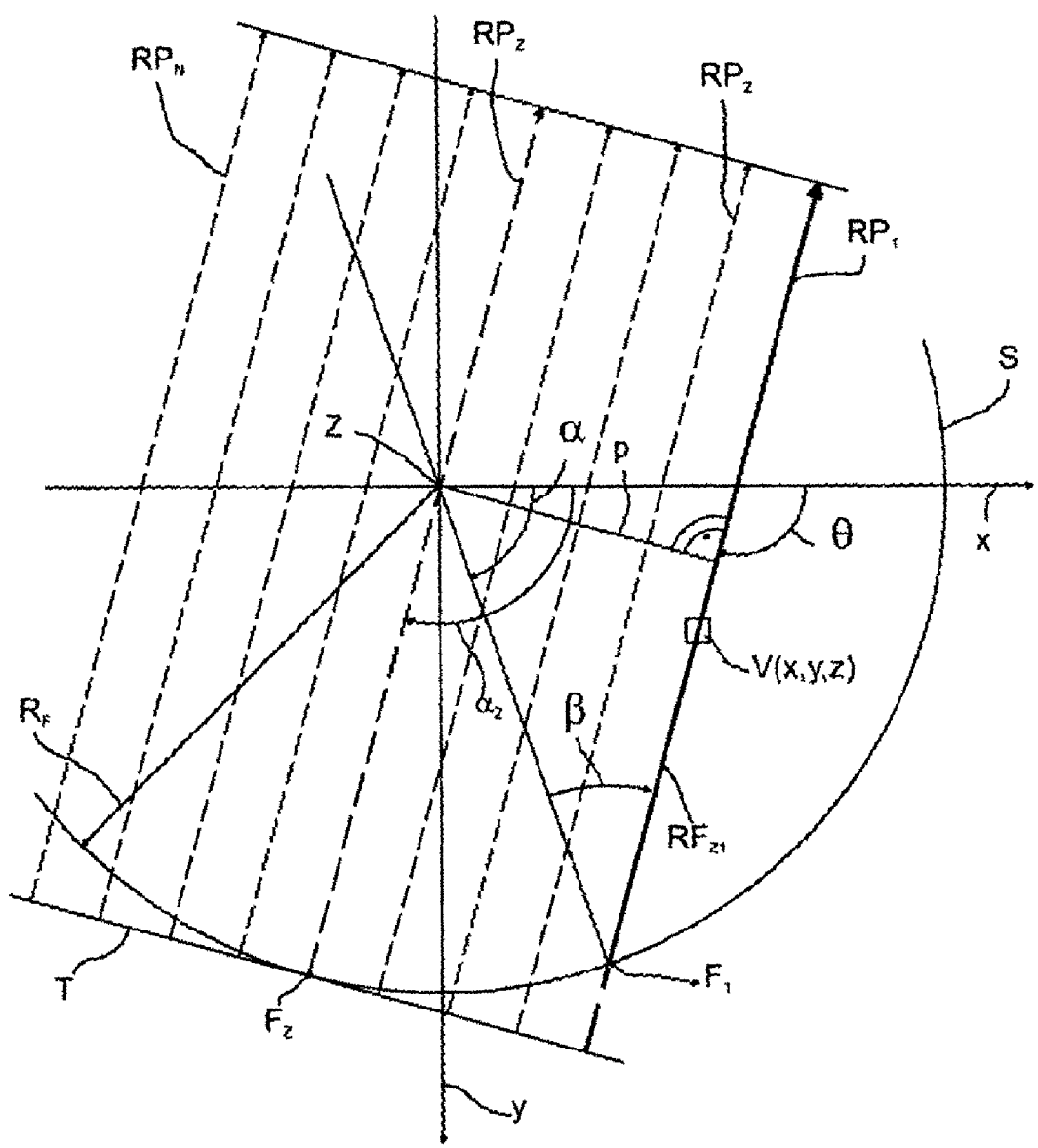
FIG. 3 shows a diagram illustrating "rebinning"

A projection in parallel beam geometry is illustrated in FIG. 3. Accordingly, all n parallel rays $RP_1$ to $RP_N$ of this projection assume the parallel fan angle $\theta$ with respect to the x axis of the coordinate system which is illustrated in FIG. 3 and coincides with that according to FIG. 1.

By using the parallel ray $RP_1$ illustrated by a continuous line in FIG. 3, the transition from fan beam to parallel been geometry will be explained below.

The parallel ray $RP_1$ originates from a projection obtained in fan beam geometry for the focal position $F_1$ located on the focal path S. The central ray $RF_{z1}$ belonging to this projection in fan beam geometry, running through the axis of rotation 14 and therefore the z axis of the coordinate system, is likewise plotted in FIG. 3. The focal position $F_1$ corresponds to the focal angle $\alpha_1$; this is the angle formed by the x axis and the central ray $RF_{z1}$. As compared with the central ray $RF_{z1}$, the ray $RP_1$ has the fan angle $\beta$. It is thus easy to see that, for the parallel fan angle $\theta$ it is true that $\theta=\alpha+\beta$.

The beam spacing p from the axis of rotation 14 or the z axis, measured at right angles to the respective parallel ray, is given by $p=R_F \sin(\beta)$.

As becomes clear by using the central ray $RP_z$ illustrated in a thickened line in FIG. 3 and extending through the axis of rotation 14 and the x axis, this ray is the central ray of a projection in fan beam geometry recorded in fan beam geometry for the focal position $F_z$ at the focal angle $\alpha_z$. Since it is true that $\beta=0$ for the central ray of a projection recorded in fan beam geometry, it becomes clear that the following is true of the case of central rays:

Depending on whether an azimuthal or complete "rebinning" is carried out, the parallel projections are present in the form P ($\alpha$, $\beta$, q)

or in the form

P ($\theta$, p, q)

where $\alpha$ is the focal angle $\beta$ is the fan angle q is the row index of the detection system corresponding to the z coordinate, ($\theta=\alpha+\beta$ is the parallel fan angle $p=R_F \sin(\beta)$ is the parallel coordinate corresponding to the ray spacing from the axis of rotation (system axis), and $R_F$ is the radius of the focal path.

In an operating mode corresponding to a first embodiment of the method according to an embodiment of the invention, which can be selected by way of the keyboard 19, the CT device described operates on the basis of projections obtained by azimuthal "rebinning". The data corresponding to these projections is filtered in the $\beta$ direction, that is to say in each case in the direction of the tangent T belonging to the focal position of the central ray of the respective parallel projection (see FIG. 3), specifically by using one of the filter kernels customary in computed tomography, e.g. a Shepp-Logan or Ramachandran-Lakshminarayanan kernel.

The parallel data filtered in this way is then backprojected in that, in the course of the backprojection, for each voxel V(x,y,z) for each $\theta\in[0, \pi]$ for the rays $P(\theta+k\pi,\tilde{\beta}, q)$ whose projection along the system axis goes through (x,y), the sum $$P_{x,y,z}(\theta) = \sum_k \sum_q W(q) \cdot h(d_{x,y,z}(\theta + k\pi, \tilde{\beta}, q)) \cdot P(\theta + k\pi, \tilde{\beta}, q)$$

is formed, where x,y,z are the coordinates of the respective voxel V(x,y,z), k is a whole number corresponding to the number of half revolutions of the focus included in the reconstruction, $\tilde{\beta}$ are the fan angle as of those rays whose projections along the system axis run through the coordinates (x,y) of the respective voxel V(x,y,z), and h is a weighting function which determines the layer thickness of the layer of the object under examination illustrated in the slice produced, and d is a function which is equal to the distance of the respective ray from the corresponding voxel V(x,y) or is dependent on the distance of the respective ray from the corresponding voxel V(x,y), and W(q) represents a weighting function which weights rays which are positioned peripherally or at least decentrally in the beam, as based on the extent in the direction of the axis of rotation, less than rays which are arranged centrally.

As a result of the selected filtering direction and as a result of the summation both over k and over q, firstly cone beam artefacts are avoided, in the interest of a high dose utilization, all the rays running through a voxel V(x,y,z) are taken into account. In addition, the positioning of the ray in the beam is also taken into account by use of appropriate weighting.

The absorption value $\mu_{x,y,z}$ associated with a voxel V(x,y,z) is obtained by means of summation over θ over at least half a revolution, that is to say by forming $$\mu_{x,y,z} = \sum_{\theta} P_{x,y,z}(\theta)$$

The CT number corresponding to the respective absorption value is determined in a conventional way from the absorption value.

In this case, different weighting functions h and different functions d can be set via the keyboard 19.

For example, a triangular or trapezoidal function is suitable as a weighting function h.

The weighting function W is represented as a function of the projection angle θ.

The function d can be the distance of the respective parallel ray from the voxel V(x,y,z) or, instead, for example the z (axial) component of this distance.

In a modification of the first operating mode described above, for the purpose of backprojection of the parallel data, the sum $$\mu_{x,y,z} = \sum_{\theta} P_{x,y,z}(\theta)$$

normalized to the sum H of the weights h $$H = \sum_{k} \sum_{q} W(q) \cdot h(d_{x,y,z}(\theta + k\pi, \tilde{\beta}, q))$$

is formed. This permits an image quality which is again improved, since the possible overemphasis of voxels which are "illuminated", that is struck by rays, in a plurality of half revolutions is eliminated and thus corresponding artefacts are avoided. This redundancy occurs during spiral scans when the relative displacement taking place per full revolution of the measuring arrangement is so low (low pitch) that voxels are irradiated repeatedly.

A second operating mode, which corresponds to a further embodiment of the method according to the invention and can be selected via the keyboard 19, differs from the first operating mode in that the CT device described does not operate on the basis of projections obtained by way of azimuthal, but by way of complete "rebinning". The data corresponding to these projections is filtered in the p direction in the case of complete "rebinning", that is to say in each case likewise in the direction of the tangent T belonging to the focal position of the central ray of the respective parallel projection (see FIG. 3).

Accordingly, for the parallel data filtered in this way in the course of the backprojection, the sum $$P_{x,y,z}(\theta) = \frac{1}{H} \sum_{k} \sum_{q} W(q) \cdot h(d_{x,y,z}(\theta + k\pi, \tilde{\beta}, q)) \cdot P(\theta + k\pi, \tilde{\beta}, q)$$

is formed, $\tilde{p}$ being the parallel coordinates of those rays whose projections along the system axis run through the coordinates (x,y) of the respective voxel V(x,y,z).

In the case of the second operating mode, too, in a modification relating to the backprojection of the parallel data, a sum normalized to the sum H of the weights h $$P_{x,y,z}(\theta) = \sum_{k} \sum_{q} W(q) \cdot h(d_{x,y,z}(\theta + k\pi, \tilde{p}, q)) \cdot P(\theta + k\pi, \tilde{p}, q)$$

is formed, namely the sum $$H = \sum_{k} \sum_{q} W(q) \cdot h(d_{x,y,z}(\theta + k\pi, \tilde{p}, q))$$

In the case of the first and second operating modes described above, a function of the method according to an embodiment of the invention is provided in which, in conjunction with a voxel V(x,y,z), all the rays whose projection along the axis of rotation of 14 or the z axis goes through x,y are considered. Whether and to what extent these rays are taken into account is determined by the weighting functions W and h and the function d.

However, the CT device can also have further operating modes which can be selected via the keyboard 19 and which correspond to those described previously. The difference is that, for a given focal position, the theoretical ray running through the respective voxel V(x,y,z) is determined. Then, taking into account the weighting function h and the function d in the sum formation, only those rays which can actually make a contribution to the sum are included in the course of the backprojection.

In the exemplary embodiments described, the relative movement between the measuring unit 1 and the mounting device 9 is in each case produced by the mounting device 9 being displaced. However, within the scope of the invention, there is also the possibility of arranging for the mounting position 9 to be fixed in position and, instead, to displace the measuring unit 1. In addition, within the scope of the invention, there is the possibility of producing the necessary relative movement by displacing both the measuring unit 1 and the mounting device 9.

Figure 4:
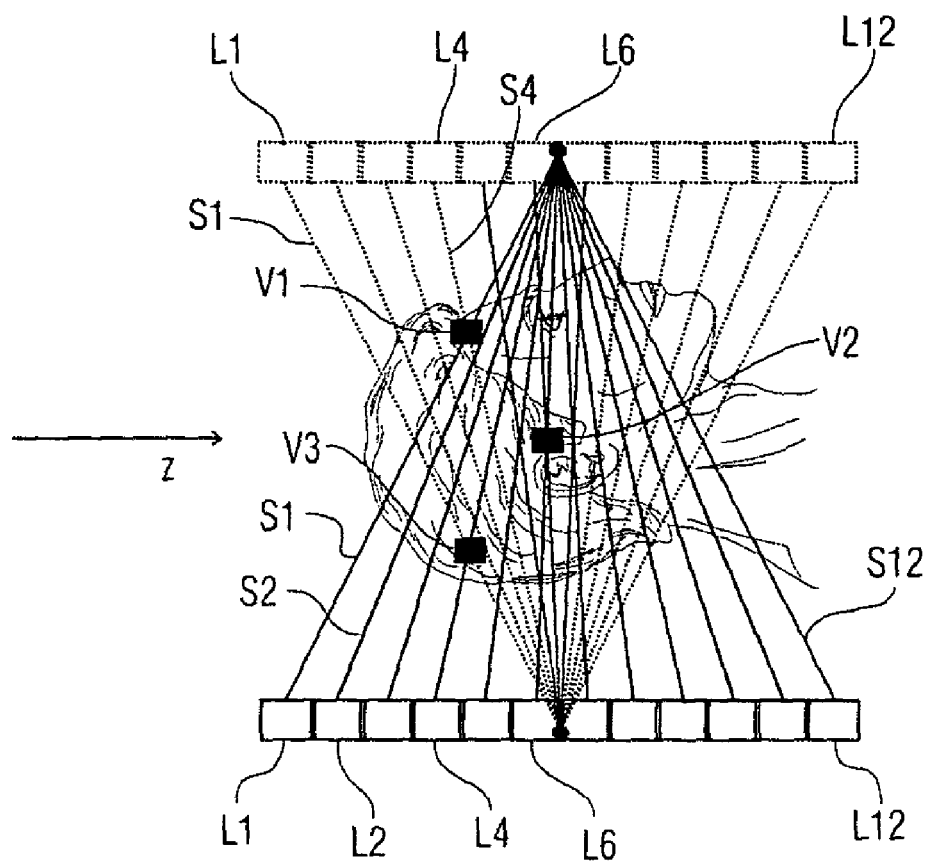
FIG. 4 shows scanning with opposite focus and detector in the beam with a rotating gantry.

In FIG. 4, the problem of weighting the rays in a 2D representation is shown, simplified and illustrated schematically. In this example, the gantry of the CT with focus and detector in the 0° position is shown by continuous lines and in the 180° position, rotated about the z axis by 180°, is shown by dots. The detector has 12 detector rows L1 to L12, which are each struck by the associated rays S1 to S12 from the beam.

It should be pointed out that the spatial dimensions shown are illustrated exaggerated with respect to the extent of the detector, in order to be able to explain the invention more clearly. The gantry shown moves on a circular path here about the z axis or system axis. Movement in the direction of the z axis does not take place.

If the voxel V2 which lies centrally in the beam is considered, this voxel will be penetrated by the central rays S4 in both positions of the gantry. According to an embodiment of the invention, the measurements from these rays are highly weighted. At the same time, in the 0° position, the voxel V1 which lies somewhat more peripherally is penetrated in the 0° position by the outer ray S1 and by the ray S4 lying further in. In accordance with the weighting according to an embodiment of the invention, the ray S1 will be given less weight than the ray S4. If the likewise peripherally arranged voxel V3 is considered, then the weighting here is reversed. Since, here, the detector is constructed with detector elements which are divided up into rows and columns in the manner of a matrix, the weighting of the rays can be coupled directly to the row number q.

Figure 5:
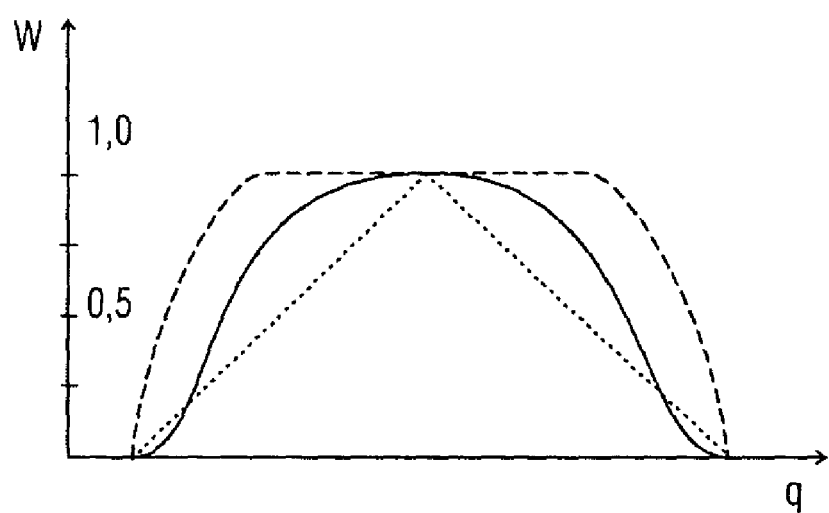
FIG. 5 shows the course of two different weighting functions W.

In FIG. 5, located below, three examples of a course according to the invention of weightings $W_q$ are illustrated. Common to all is the greater weighting of the central rays with respect to the outer rays. However, the functions are different. The dotted line represents a course which drops off linearly on either side of the centre, the dashed line results in identical weighting over a large central region with a tendency to drop off rapidly at the periphery, and the continuous line shows a bell-like course which permits a gentle transition between the extreme values 0 and 1.

Figure 6:
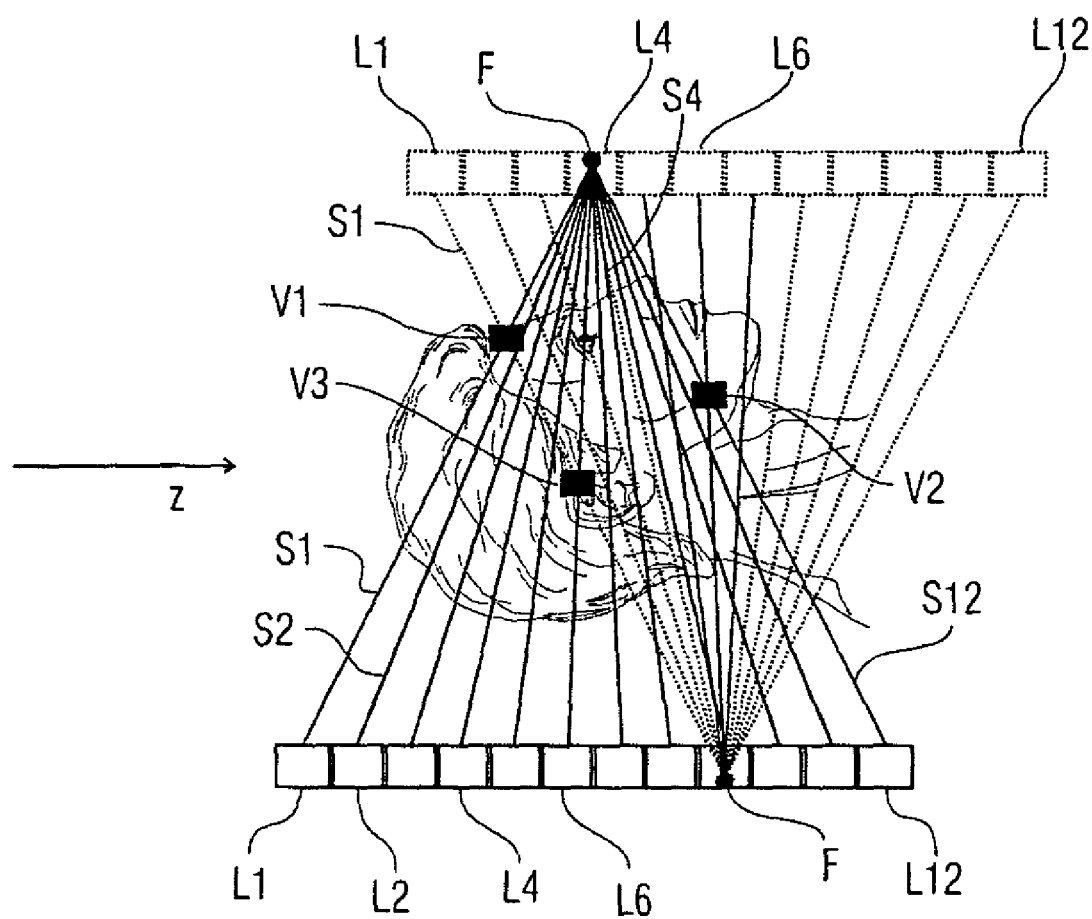
FIG. 6 shows scanning with opposite focus and detector in the beam with the gantry rotating and moving in the z direction.

FIG. 6 shows CT beams from a gantry of a spiral CT respectively in the 0° position and adjacent 180° position. In accordance with the essence of the spiral CT, these positions are offset in relation to each other in addition to the rotation in the z direction.

In this illustration, the voxel V1 is penetrated by the ray S1 both in the 0° position and in the 180° position. In accordance with this decentral position of the ray S1 and the associated detector row L1 located on the outside in the detector, these two measurements are weighted lowly. By contrast, the voxel V2 in the 0° position is penetrated by the ray S12 located decentrally, which is weighted lowly in this position for the voxel V2. But in the 180° position, it is penetrated by the central ray S6, which is weighted highly for this voxel V2. In accordance with the position of the rays S1 in the 0° and 180° positions, these rays are both weighted lowly in relation to the voxel V1. Overall, as a result of this additional weighting W illustrated here, the result is a substantial improvement in the image quality.

It should be pointed out that the conical x-ray beam has a rectangular cross section in the exemplary embodiment described here, but other cross-sectional geometries are also possible within the scope of the invention.

In connection with the exemplary embodiments described above, CT devices of the third generation are used, that is to say the x-ray source and the detector system are displaced jointly about the system axis during the image generation. However, the embodiments of invention can also be used in connection with CT devices of the fourth generation for example, in which only the x-ray source is displaced about the system axis and interacts with a stationary detector ring, if the detector system is a multi-row array of detector elements.

The method according to the embodiments of invention can also be used in CT devices of the fifth generation, that is to say CT devices in which the X-radiation originates from a plurality of foci of one or more x-ray sources displaced about the system axis, and not just from one focus, if the detector system has a multi-row array of detector elements.

The CT devices used in connection with the exemplary embodiments described above have a detector system of detector elements arranged in the manner of an orthogonal matrix. However, the embodiments of invention can also be used in connection with CT devices whose detector system has a non-one-dimensional array with detector elements arranged in another way.

The exemplary embodiments described above relate to the medical application of the method according to the embodiments of the invention. However, the invention can also be applied outside medicine, for example in checking luggage or in material examination.

What is claimed is:

1. A method of creating images in computer tomography, comprising:
   rotating at least one focus, to scan an object under examination with a beam originating from the at least one focus, relative to the object on at least one focal path running around the object, wherein a detector array including a plurality of distributed detector elements arranged in rows and lines and the detector array is adapted to detect rays of the beam and is adapted to supply initial data representing an attenuation of the rays passing through the object under examination;
   filtering the initial data, wherein before the filtering, the initial data is obtained in fan beam geometry and rebinned into parallel beam geometry, and the filtering is carried out in a direction of a tangent to the at least one focal path belonging to the respective focal position;
   backprojecting the filtered initial data, three-dimensionally, to produce at least one slice of a layer of the object having a layer thickness, the slice representing radiation absorption values of voxels belonging to the layer of the object, wherein, during the backprojection, the rays are weighted as a function of corresponding position in the beam with a weighting function representing a smooth function of the row number, the weighting function having a value of one for rays to at least one centrally located detector row, tending to zero for rays to detector rows towards an edge of the detector rows, and zero for rays to detector rows at the edge of the detector rows.

2. The method as claimed in claim 1, wherein the beam includes an extent in the direction of rotation and an extent in the direction of the axis of rotation, and wherein arranged centrally in the beam, as based on the extent of the beam in the direction of the axis of rotation, are weighted to a relatively greater extent than the rays arranged close to the edge in the beam, as based on the extent of the beam in the direction of the axis of rotation.

3. The method as claimed in claim 1, wherein the rebinning includes,
   converting, before filtering, the initial data obtained in fan beam geometry in the form of rays $P(\alpha,\beta,q)$ into parallel data present in parallel beam geometry in the form of rays $P(\theta,\beta,q)$ or $P(\theta,p,q)$, where
   $\alpha$ is the focal angle
   $\beta$ is the fan angle
   q is the row index of the detector system corresponding to the z coordinate,
   $\theta=\alpha+\beta$ is the parallel fan angle,
   $p=R_F \sin(\beta)$ is the parallel coordinate corresponding to the distance of the ray from the axis of rotation (system axis), and
   $R_F$ is the radius of the focal path.

4. The method as claimed in claim 3, wherein the backprojection of the parallel data is carried out and, in the course of the backprojection for each voxel V(x,y,z), for each $\theta\in[o,\pi]$ for the rays $P(\theta+k\pi,\tilde{\beta},q)$ and $P(\theta+k\pi,\tilde{p},q)$ whose projection along the system axis goes through (x,y), the sum $$P_{x,y,z}(\theta) \sum_k \sum_q W \cdot h\left(d_{x,y,z}\left(\theta+k\pi, \left\{\begin{matrix}\tilde{p}\\ \tilde{\beta}\end{matrix}\right\}, q\right)\right) \cdot P\left(\theta+k\pi, \left\{\begin{matrix}\tilde{p}\\ \tilde{\beta}\end{matrix}\right\}, q\right)$$

is formed, where x,y,z are the coordinates of the respective voxel V(x,y,z), k is a whole number corresponding to the number of half revolutions of the focus included in the reconstruction, $\tilde{p}$ are the parallel coordinates of those rays whose projections along the system axis run through the coordinates (x,y) of the respective voxel V(x,y,z), $\tilde{\beta}$ are the fan angles of those rays whose projections along the system axis run through the coordinates (x,y) of the respective voxel V(x,y,z), h is a weighting function determining the layer thickness of the layer of the object under examination represented in the slice produced, d is a function which is equal to the distance of the respective ray from the corresponding voxel V(x,y) or is dependent on the distance of the respective ray from the corresponding voxel V(x,y), and W represents a weighting function which weights rays with a large parallel fan angle $\theta$ less than rays with a small parallel fan angle $\theta$.

5. The method as claimed in claim 4, wherein, during the backprojection of the parallel data, the sum $$H = \sum_k \sum_q W \cdot h\left(d_{x,y,z}\left(\theta+k\pi, \left\{\begin{matrix}\tilde{p}\\ \tilde{\beta}\end{matrix}\right\}, q\right)\right)$$

normalized to the sum H of the weights h $$P_{x,y,z}(\theta) = \frac{1}{H}\sum_k \sum_q W \cdot h\left(d_{x,y,z}\left(\theta+k\pi, \left\{\begin{matrix}\tilde{p}\\ \tilde{\beta}\end{matrix}\right\}, q\right)\right) \cdot P\left(\theta+k\pi, \left\{\begin{matrix}\tilde{p}\\ \tilde{\beta}\end{matrix}\right\}, q\right)$$

is formed.

6. The method as claimed in claim 5, wherein the weighting function represents a function of the parallel fan angle with $W(\theta+k\pi)$.

7. The method as claimed in claim 4, wherein the detector array includes detector elements arranged in the manner of rows, and the weighting function represents a function of the row number W(q).

8. The method as claimed in claim 1, wherein the focal path is a circular path.

9. The method as claimed in claim 1, wherein the focal path is a spiral path which is brought about by the focus being moved about the system axis on a circular path and, at the same time, a relative movement between focus and object under examination in the direction of the system axis taking place.

10. The method as claimed in claim 1, wherein the detector elements on the detector array are arranged distributed in the manner of a matrix.

11. A non-transitory computer-readable medium comprising computer executable instructions configured to cause a computer to perform the method of claim 1.

12. A non-transitory computer-readable medium having code portions embodied thereon that, when read by a processor, cause said processor to perform the method of claim 1.

13. The method of claim 1, wherein the weighting function is independent of a rotational position of a radiation source configured to emit the rays of the beam.

14. A computed tomography (CT) device for scanning an object under examination, comprising:
    means for scanning the object, including at least one focus from which a beam originates;
    a detector array including a plurality of distributed detector elements arranged in rows and lines, wherein the at least one focus is movable relative to the object on at least one focal path running around the object and wherein the detector array is adapted to supply detected data representing an attenuation of the rays passing through the object, the detected data configured to be obtained in fan beam geometry and rebinned into parallel beam geometry;
    means for filtering the detected data, the means for filtering being configured to carryout filtering in the direction of a tangent to the at least one focal path belonging to the respective focal position;
    means for backprojecting the filtered data, three-dimensionally, to produce at least one slice of a layer of the object having a layer thickness, the slice representing radiation absorption values of voxels belonging to the layer, wherein, during the backprojection, the rays are weighted as a function of corresponding position in the beam, with a weighting function representing a smooth function of the row number, the weighting function having a value of one for rays to at least one centrally located detector row, tending to zero for rays to detector rows towards an edge of the detector rows, and zero for rays to detector rows at the edge of the detector rows; and
    means for collecting the data.

15. The CT device as claimed in claim 14, wherein at least one of the means for scanning, the means for filtering and the means for backprojecting is at least partly implemented by at least one of programs and program modules.

* * * * *